United States Patent
Garcia et al.

(10) Patent No.: US 11,645,577 B2
(45) Date of Patent: May 9, 2023

(54) DETECTING CHANGES BETWEEN DOCUMENTS USING A MACHINE LEARNING CLASSIFIER

(71) Applicant: International Business Machines Corporation, Armonk, NY (US)

(72) Inventors: Luis Alexandro Garcia, El Paso, TX (US); Adam T. Clark, Mantorville, MN (US)

(73) Assignee: International Business Machines Corporation, Armonk, NY (US)

(*) Notice: Subject to any disclaimer, the term of this patent is extended or adjusted under 35 U.S.C. 154(b) by 929 days.

(21) Appl. No.: 16/549,227

(22) Filed: Aug. 23, 2019

(65) Prior Publication Data
US 2020/0372405 A1 Nov. 26, 2020

Related U.S. Application Data

(60) Provisional application No. 62/850,590, filed on May 21, 2019.

(51) Int. Cl.
| | | |
|---|---|---|
| *G06N 20/00* | (2019.01) | |
| *G16H 10/20* | (2018.01) | |
| *G06F 16/93* | (2019.01) | |

(52) U.S. Cl.
CPC .......... *G06N 20/00* (2019.01); *G06F 16/93* (2019.01); *G16H 10/20* (2018.01)

(58) Field of Classification Search
None
See application file for complete search history.

(56) References Cited

U.S. PATENT DOCUMENTS

| | | | |
|---|---|---|---|
| 8,949,242 B1 | 2/2015 | Lin et al. | |
| 11,226,720 B1* | 1/2022 | Vandivere | G06F 3/0482 |
| 11,423,220 B1* | 8/2022 | Cobb | G06F 16/93 |
| 2010/0223239 A1 | 9/2010 | Madsen et al. | |
| 2011/0112873 A1 | 5/2011 | Allen et al. | |
| 2015/0100382 A1 | 4/2015 | Malhotra et al. | |
| 2019/0266196 A1* | 8/2019 | Boyce | G06Q 50/188 |
| 2019/0385054 A1* | 12/2019 | Zuev | G06F 40/30 |
| 2020/0175095 A1* | 6/2020 | Morariu | G06V 30/414 |
| 2020/0293616 A1* | 9/2020 | Nelson | G06Q 10/101 |
| 2021/0209551 A1* | 7/2021 | Navarra | G06F 16/93 |

FOREIGN PATENT DOCUMENTS

| | | |
|---|---|---|
| CN | 104580099 A | 4/2015 |
| CN | 105589813 B | 12/2018 |

* cited by examiner

*Primary Examiner* — Toan H Vu
(74) *Attorney, Agent, or Firm* — Edell, Shapiro & Finnan, LLC

(57) ABSTRACT

A present invention embodiment detects changes between documents. A machine learning classifier is trained with one or more sections within an initial document to learn classifications for the sections. The one or more sections of the initial document serve as the classifications. One or more second sections of a second document are applied to the machine learning classifier to classify the one or more second sections. The one or more second sections are mapped to the one or more sections of the initial document based on the classification of the one or more second sections.

17 Claims, 6 Drawing Sheets

Clinical Trial A:

~~Female patients must not be pregnant;~~

Patients must be ~~at least~~ between 18 ~~and 55~~ years ~~old of age~~;

Patients must be ~~enrolled~~ registered less than 21 days prior to the end of chemotherapy; and ~~Bilirubin levels < 2x ULN~~

Adequate renal~~, hematologic, and coagulation~~ function~~;~~.

FIG.6

DETECTING CHANGES BETWEEN DOCUMENTS USING A MACHINE LEARNING CLASSIFIER

CROSS REFERENCE TO RELATED APPLICATIONS

This application claims priority to U.S. Provisional Patent Application Ser. No. 62/850,590, entitled "DETECTING CHANGES BETWEEN DOCUMENTS USING A MACHINE LEARNING CLASSIFIER" and filed on May 21, 2019, the disclosure of which is incorporated herein by reference in its entirety.

BACKGROUND

1. Technical Field

Present invention embodiments relate to document management systems, and more specifically, to employing a machine learning classifier to detect changes between documents.

2. Discussion of the Related Art

Documents may contain various different sections. For example, a policy document is a document with various statements defining conditions for some entity to match the policy. A typical example is a medical clinical trial that has a list of acceptance criteria that defines characteristics of patients to be accepted into the medical clinical trial.

When working with these policy documents, it is often necessary to track each individual requirement statement, and maintain metadata associated with that requirement statement. Metadata may include any data, such as a version number, a modification date, any overrides necessary for that specific criterion, etc.

As a document changes and evolves over time, and the language used for the sections changes, it is difficult to determine which individual section from an updated document maps to some version of the section of a previous document.

SUMMARY

According to one embodiment of the present invention, a system detects changes between documents and comprises at least one processor. A machine learning classifier is trained with one or more sections within an initial document to learn classifications for the conditions. The one or more sections of the initial document serve as the classifications. One or more second sections of a second document are applied to the machine learning classifier to classify the one or more second sections. The one or more second sections are mapped to the one or more sections of the initial document based on the classification of the one or more second sections. Embodiments of the present invention further include a method and computer program product for detecting changes between documents in substantially the same manner described above.

BRIEF DESCRIPTION OF THE DRAWINGS

Generally, like reference numerals in the various figures are utilized to designate like components.

FIG. 6 is an illustration of an example display presenting changes to sections across documents according to an embodiment of the present invention.

DETAILED DESCRIPTION

Figure 1:
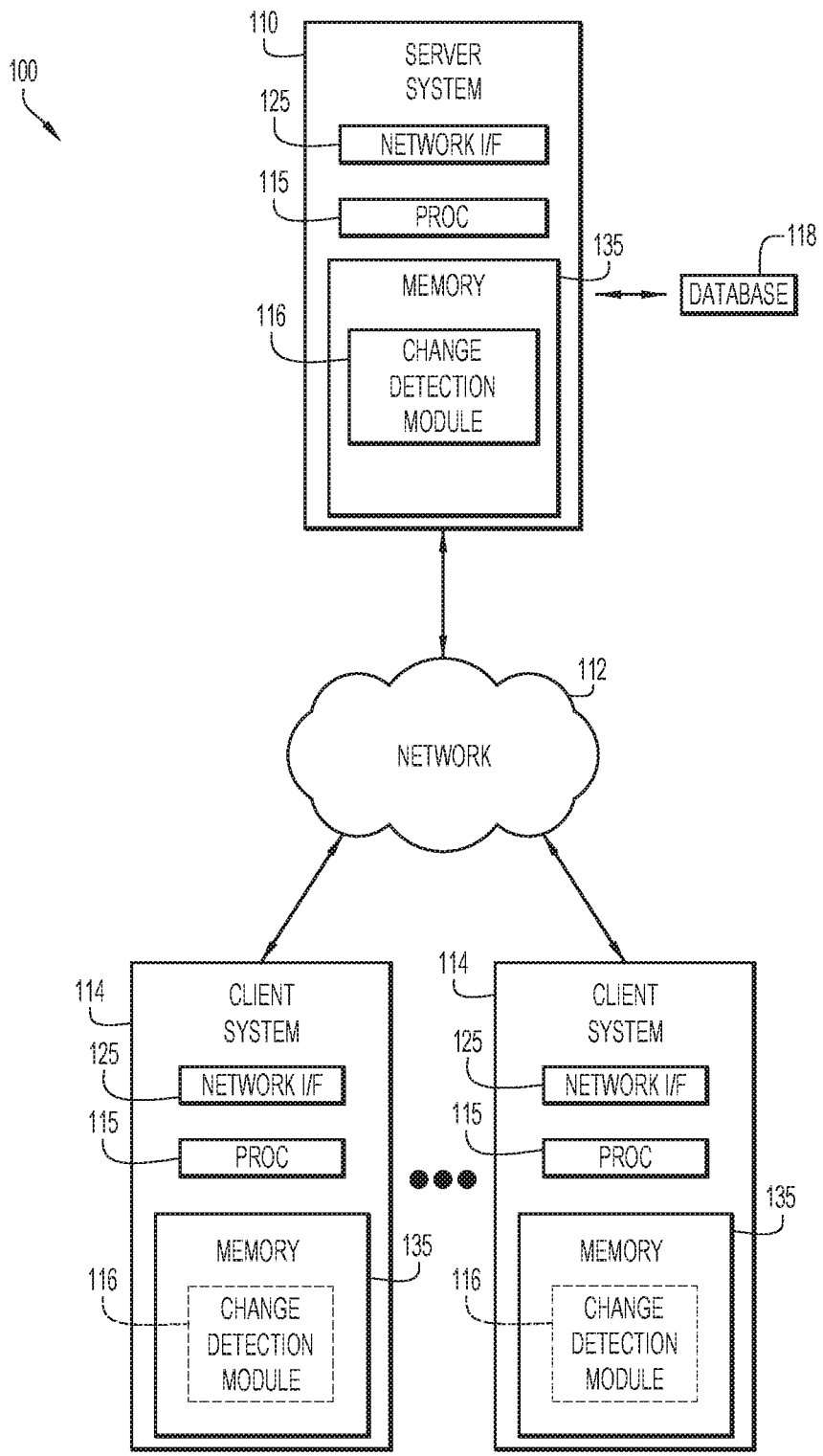
FIG. 1 is a diagrammatic illustration of an example computing environment according to an embodiment of the present invention.

Present invention embodiments pertain to detecting changes to documents using a machine learning classifier. The documents may include sections, where present invention embodiments may detect and/or track changes to the document sections. For example, an embodiment of the present invention may detect changes to requirements or criteria of a policy (e.g., medical clinical trial, etc.) between documents containing the policy. As a policy document changes and evolves over time, and the language used for each criterion changes, it is hard to determine which individual criterion from an updated policy document maps to a previous policy document. By way of example, two versions of a document including the same clinical trial and acceptance criteria (e.g., where ULN indicates an upper limit of normal) may include:

Clinical Trial A, Version v1:
  a) Patients must be at least 18 years old;
  b) Adequate renal function;
  c) Patients must be enrolled less than 21 days prior to end of chemotherapy; and
  d) Bilirubin levels <2× ULN.

Clinical Trial A, Version v2:
  a) Female patients must not be pregnant;
  b) Patients must be between 18 and 55 years of age;
  c) Patients must be registered less than 21 days prior to end of chemotherapy; and
  d) Adequate renal, hematologic, and coagulation function.

In order to track a lifespan of individual acceptance criteria statements and their evolution throughout time, the following changes to identify in the example include:

1. Criterion a) in Version v2 is a brand-new criterion that was not present in Version v1;
  2. Criterion b) in Version v2 corresponds to criterion a) in Version v1 (even though the wording changed moderately);
  3. Criterion c) in Version v2 corresponds to criterion c) in Version v1 (even though the wording changed slightly);
  4. Criterion d) in Version v2 corresponds to criterion b) in Version v1 (even though the wording changed significantly); and
  5. Criterion d) in Version v1 is deleted from Version v2.

An embodiment of the present invention relies on a natural language (NL) classifier to map sections (e.g., policy requirements, etc.) between documents. Generally, a natural language (NL) classifier uses machine learning algorithms or models to return a set of classifications for given input or text. The classifications are previously created and the classifier is trained to learn or recognize input or text that match those classifications.

For example, a natural language (NL) classifier may be trained to recognize an intent of a customer review:

"I really loved this movie"—Classification: Positive;
"This movie was awesome!"—Classification: Positive;
"Excellent performances!"—Classification: Positive;
"I really hated this movie"—Classification: Negative;
"What an awful movie"—Classification: Negative; and
"Wasted time"—Classification: Negative.

Based on the above text and classifications, a natural language (NL) classifier may be trained to classify intent of customer reviews as positive or negative. Typically, plural examples or training sets are used to train the natural language (NL) classifier to learn or recognize text from each of the classifications. However, the natural (NL) classifier of present invention embodiments utilizes a single instance to train the classifier for a classification as described below.

An embodiment of the present invention uses a natural language (NL) classifier to map sections (e.g., criteria of a policy, etc.) from a new version of a document to sections (e.g., criteria, etc.) from a prior or baseline document. Each of the original sections in the baseline document is both a classification and a sole training set or text to train the natural language (NL) classifier. Thus, only a single instance may be used to train the classifier for a classification. When sections from the new document are applied to the natural language (NL) classifier, the natural language (NL) classifier classifies the sections from the new document as one of the sections from the original document, thereby mapping the sections from the new document to the corresponding original version.

An example computing environment for use with present invention embodiments is illustrated in FIG. 1. Specifically, the computing environment includes one or more server systems 110, and one or more client or end-user systems 114. Server systems 110 and client systems 114 may be remote from each other and communicate over a network 112. The network may be implemented by any number of any suitable communications media (e.g., wide area network (WAN), local area network (LAN), Internet, Intranet, etc.). Alternatively, server systems 110 and client systems 114 may be local to each other, and communicate via any appropriate local communication medium (e.g., local area network (LAN), hardwire, wireless link, Intranet, etc.).

Client systems 114 enable users to submit documents (e.g., documents containing policies and corresponding requirements or criteria, etc.) to server systems 110 to detect changes to sections across the documents. The server systems include a change detection module 116 to detect changes to the document sections as described below. A database system 118 may store various information for the analysis (e.g., documents, classifier information, etc.). The database system may be implemented by any conventional or other database or storage unit, may be local to or remote from server systems 110 and client systems 114, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents and analysis, and may provide reports including analysis results (e.g., changes, markings, etc.).

Server systems 110 and client systems 114 may be implemented by any conventional or other computer systems preferably equipped with a display or monitor, a base (e.g., including at least one hardware processor 115 (e.g., microprocessor, controller, central processing unit (CPU), etc.), one or more memories 135 and/or internal or external network interfaces or communications devices 125 (e.g., modem, network cards, etc.)), optional input devices (e.g., a keyboard, mouse or other input device), and any commercially available and custom software (e.g., server/communications software, change detection module 116, browser/interface software, etc.).

Alternatively, one or more client systems 114 may analyze documents to determine changes to sections across the documents when operating as a stand-alone unit. In a stand-alone mode of operation, the client system stores or has access to the data (e.g., documents, etc.), and includes change detection module 116 to detect changes to the document sections as described below. The graphical user (e.g., GUI, etc.) or other interface (e.g., command line prompts, menu screens, etc.) solicits information from a corresponding user pertaining to the desired documents and analysis, and may provide reports including analysis results.

Change detection module 116 may include one or more modules or units to perform the various functions of present invention embodiments described below. The various modules (e.g., change detection module 116, etc.) may be implemented by any combination of any quantity of software and/or hardware modules or units, and may reside within memory 135 of the server and/or client systems for execution by processor 115.

Figure 2:
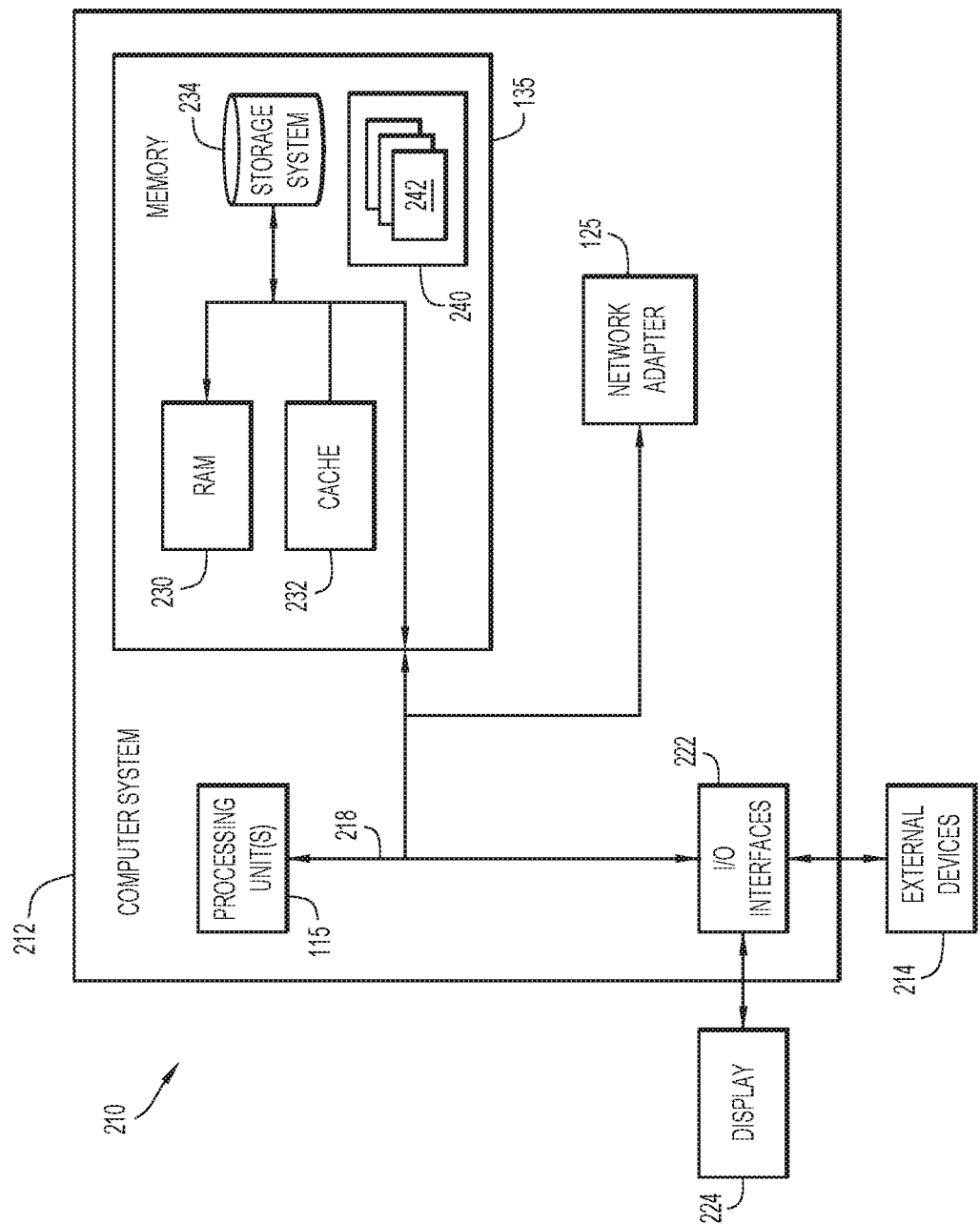
FIG. 2 is a block diagram of an example computing device according to an embodiment of the present invention.

Referring now to FIG. 2, a schematic of an example of a computing device 210 of computing environment 100 (e.g., implementing server system 110 and/or client system 114) is shown. The computing device is only one example of a suitable computing device for computing environment 100 and is not intended to suggest any limitation as to the scope of use or functionality of embodiments of the invention described herein. Regardless, computing device 210 is capable of being implemented and/or performing any of the functionality set forth herein.

In computing device 210, there is a computer system 212 which is operational with numerous other general purpose or special purpose computing system environments or configurations. Examples of well-known computing systems, environments, and/or configurations that may be suitable for use with computer system 212 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules, being executed by a computer system. Generally, program modules may include routines, programs, objects, components, logic, data structures, and so on that perform particular tasks or implement particular abstract data types.

As shown in FIG. 2, computer system 212 is shown in the form of a computing device. The components of computer system 212 may include, but are not limited to, one or more processors or processing units 115, a system memory 135, and a bus 218 that couples various system components including system memory 135 to processor 115.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 135 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 135 may include at least one program product having a set (e.g., at least one) of program modules that are configured to carry out the functions of embodiments of the invention.

Program/utility 240, having a set (at least one) of program modules 242 (e.g., change detection module 116, etc.) may be stored in memory 135 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 125. As depicted, network adapter 125 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
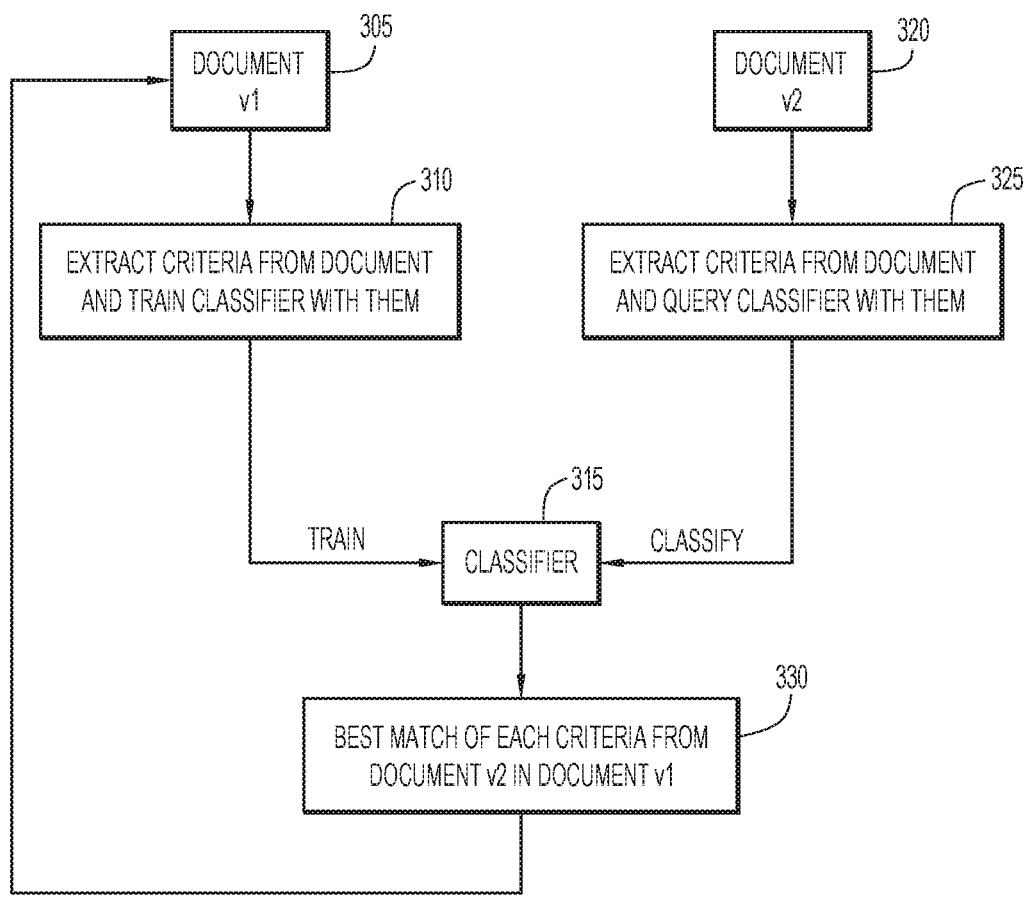
FIG. 3 is a flow diagram of a manner of detecting changes to sections across documents according to an embodiment of the present invention.

A manner of detecting changes to document sections across documents (e.g., via change detection module 116, and server system 110 and/or client system 114) according to an embodiment of the present invention is illustrated in FIG. 3. Initially, a natural language (NL) classifier 315 is created for each individual document 305 (e.g., a document containing various sections, a document containing sections in the form of criteria for a medical clinical trial or other policy, etc.). The classifier is trained at operation 310 using each individual document section as both a classification and a single instance of training data or text for that classification.

A new version of the document 320 (e.g., containing modified document sections, containing sections in the form of criteria for a medical clinical trial or other policy, etc.) is received and each individual section is extracted from new document 320 at operation 325. Each individual section is provided to classifier 315, and for each of those sections, the classifier determines and returns at operation 330 the classification that is most likely to be the best match in document 305. The best match refers to the section in document 305 that is more similar to the new version of the section in document 320. A section of document 305 is determined to be a best match when the section satisfies a pre-determined threshold of similarity. The threshold of similarity indicates when the section of document 320 is considered a new version of the existing section in document 305. The threshold of similarity may be configurable and, by way of example, may be a value indicating at least 70% similarity (e.g., a value equal to or greater than 70%). However, any suitable threshold value or threshold range may be utilized. In cases where plural prior sections from document 305 satisfy the threshold of similarity, a selection is made as to whether the best result from classifier 315 is respected, or manual interpretation is needed.

If classifier 315 does not return a result satisfying the threshold of similarity, this indicates the section of document 320 is a brand-new section in the new document (e.g., a new criterion for a medical clinical trial or other policy, etc.).

In addition, all the classifications that have already been matched to some input are tracked, and left-over or unmatched classifications at the completion of the classification (or matching process) are considered sections of document 305 that were removed in the new document.

Individual sections (e.g., criterion, etc.) are evaluated and mapped to their predecessor in a predominantly isolated manner. However, when disputes occur (e.g., two or more new sections match a prior section) or sections are unable to adequately map to prior sections, the entire document (e.g., medical clinical trial or other policy, etc.) may be evaluated as being successfully mapped. This holistic evaluation is valuable as a measurement of the success as a system.

For a corpus of documents with plural initial documents each having a series of revision documents (e.g., the corpus of documents includes multiple medical clinical trials or other policies, etc.), one classifier per each document with a revision document series is created, and the classifiers are applied individually for the documents of each revision series (e.g., clinical medical trial, etc.) and for each document section.

Figure 4:
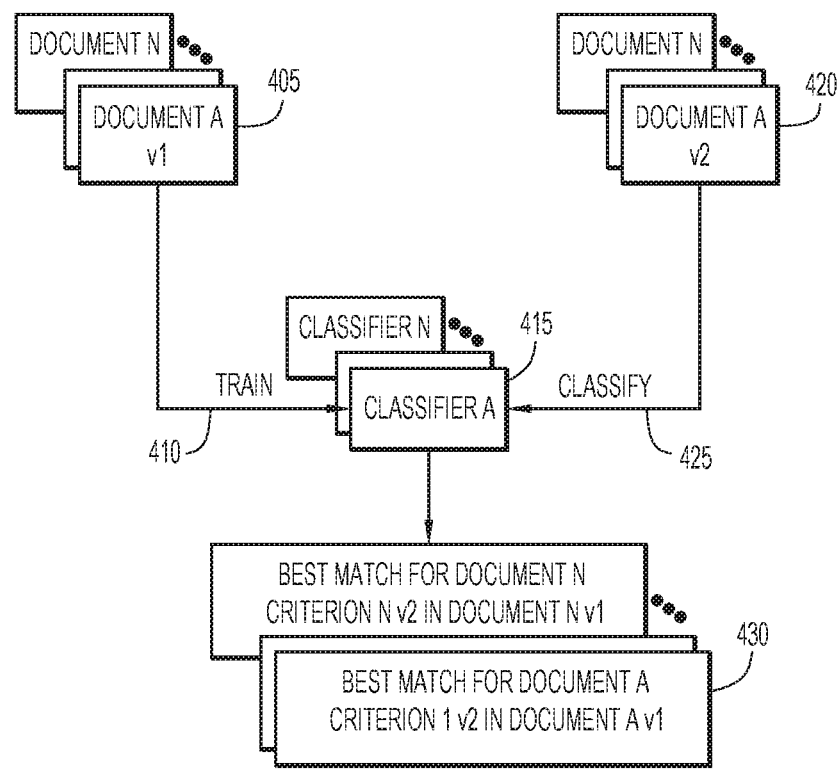
FIG. 4 is a flow diagram of a manner of detecting changes to sections of plural documents across corresponding series of revision documents according to an embodiment of the present invention.

A manner of detecting changes to sections of plural documents across corresponding series of revision documents (e.g., via change detection module 116, and server system 110 and/or client system 114) according to an embodiment of the present invention is illustrated in FIG. 4. Initially, a natural language (NL) classifier 415A-N is created for each initial document 405A-N (e.g., each document 405A-N contains various sections, each document 405A-N may contain sections in the form of criteria for a medical clinical trial or other policy, etc.). Each classifier 415A-N is trained at operation 410 using each individual section of the corresponding initial document 405A-N (e.g., a classifier 415A is trained based on sections in document 405A, etc.) as both a classification and a single instance of training data or text for that classification.

A new version of the documents 420A-N (e.g., containing modified document sections, containing sections in the form of criteria for a medical clinical trial or other policy, etc.) is received and each individual section is extracted from a corresponding new document 420A-N at operation 425. Each individual section of documents 420A-N is provided to a corresponding classifier 415A-N (e.g., an individual section from document 420A is provided to classifier 415A, etc.), and for each of those sections, the corresponding classifier determines and returns at operation 430 the classification that is most likely to be the best match in corresponding document 405A-N. The best match refers to the section in the document 405A-N that is more similar to the new version of the section in corresponding document 420A-N. A section of document 405A-N is determined to be a best match when the section satisfies a pre-determined threshold of similarity. The threshold of similarity indicates when the section of document 420A-N is considered a new version of the existing section in corresponding document 405A-N. The threshold of similarity may be configurable and, by way of example, may be a value indicating at least 70% similarity (e.g., a value equal to or greater than 70%). However, any suitable threshold value or threshold range may be utilized. In cases where plural prior sections from document 405A-N satisfy the threshold of similarity, a selection is made as to whether the best result from classifier 415A-N is respected, or manual interpretation is needed.

If classifier 415A-N does not return a result satisfying the threshold of similarity, this indicates the section of corresponding document 420A-N is a brand-new section in the new document (e.g., a new criterion for a medical clinical trial or other policy, etc.).

In addition, all the classifications that have already been matched to some input are tracked, and left-over or unmatched classifications at the completion of the classification (or matching process) are considered sections of document 405A-N that were removed in the new document.

Individual sections (e.g., criterion, etc.) are evaluated and mapped to their predecessor in a predominantly isolated manner. However, when disputes occur (e.g., two or more new sections match a prior section) or sections are unable to adequately map to prior sections, the entire document (e.g., medical clinical trial or other policy, etc.) may be evaluated as being successfully mapped. This holistic evaluation is valuable as a measurement of the success as a system.

Figure 5:
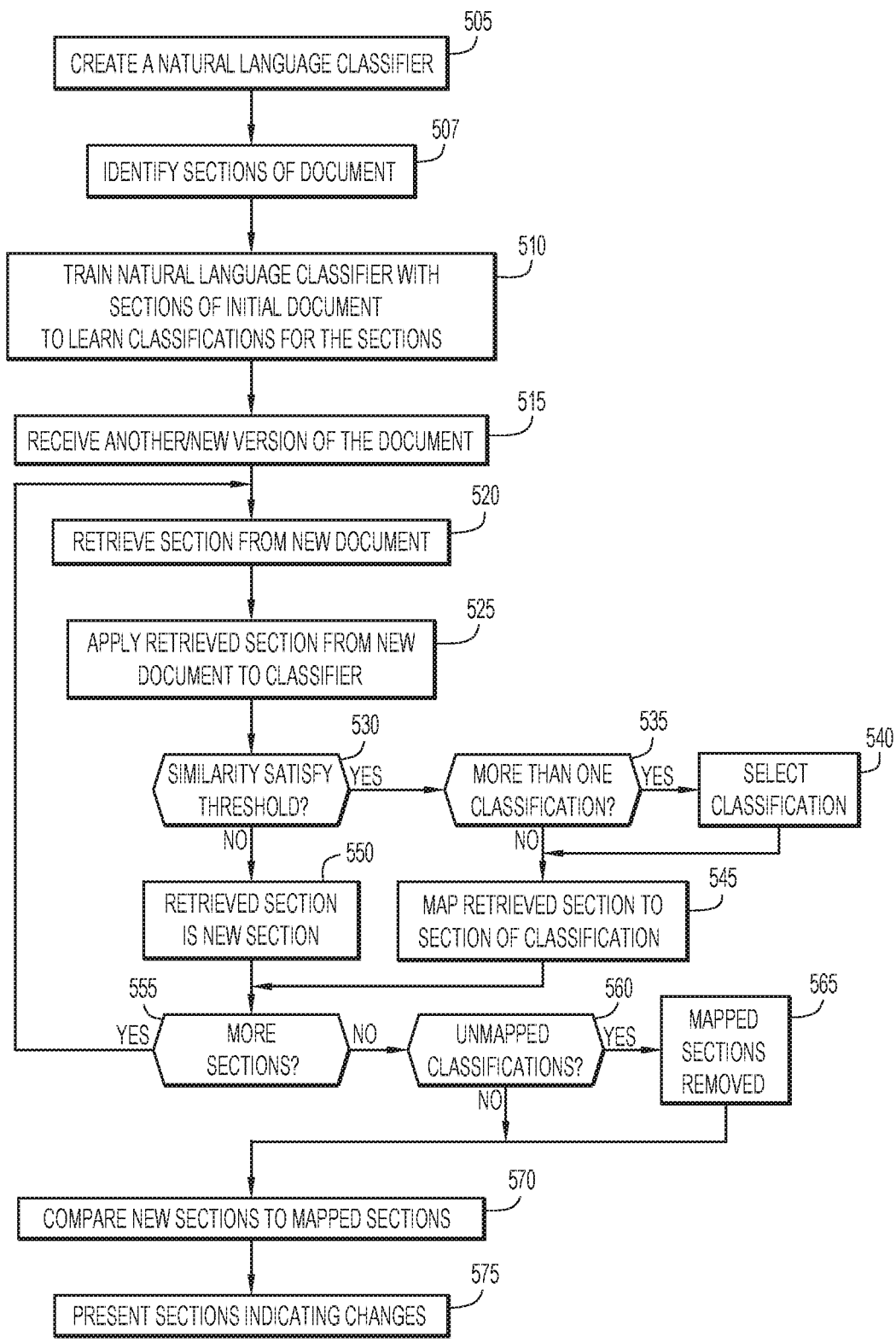
FIG. 5 is a procedural flowchart illustrating a manner of detecting and presenting changes across documents according to an embodiment of the present invention.

A manner of detecting and presenting changes across documents (e.g., via change detection module 116, and server system 110 and/or client system 114) according to an embodiment of the present invention is illustrated in FIG. 5. Initially, a natural language (NL) classifier is created for an initial document at operation 505. The document may contain one or more sections, where each section may represent some portion of content (e.g., sentence, paragraph, predefined sections, based on section headings, etc.). For example, the document may include a policy document containing one or more criteria, requirements, or conditions to satisfy a policy. A policy document, by way of example, may be for a medical clinical trial and include one or more criteria for patients to be accepted or admitted into the medical clinical trial. The document is examined at operation 507 to identify the individual sections of the document (e.g., where each identified section may represent some portion of content, such as a sentence, a paragraph, predefined sections, sections based on section headings, etc.).

The classifier is trained at operation 510 using the identified sections that serve as both a classification and as a single instance of training data or text to enable the classifier to learn that classification. The classifier is trained to produce for a received section a classification and a corresponding score (e.g., indicating a similarity of the received section to a prior version of the section, indicating a confidence of the classification, etc.). The classifier may be of any conventional or other type of classifier and employ any machine learning models (e.g., linear classifiers, such as logistic regression and naive Bayes classifier, support vector machines, decision trees, boosted trees, random forest, neural networks, nearest neighbor, etc.).

A new document (e.g., containing modified document sections, containing sections in the form of criteria for a medical clinical trial or other policy, etc.) is received at operation 515. The new document may contain new sections (e.g., criterion or conditions for a new policy, etc.) and/or an updated version of the sections (e.g., criterion or conditions for a policy) in a prior document. An individual section for the policy is retrieved from the new document at operation 520, and applied to the classifier at operation 525. The classifier determines and returns one or more classifications for the retrieved section and corresponding scores indicating a similarity of corresponding sections from the initial document to the retrieved section. Since the classification refers to a section in the initial document, the classifier basically determines the section of the initial document corresponding to the retrieved section for the new document despite any changes or modifications to the content of the section in the new document, and/or to the order of the section in the new document.

The scores are compared to a threshold at operation 530 to determine when the received section is considered a new version of a section in the initial document. The threshold may be configurable and, by way of example, may be a value indicating at least 70% similarity (e.g., a value equal to or greater than 70%). However, any suitable threshold value or threshold range may be utilized.

Further, the received section may be considered a new version of the initial document when the score for the received section (with respect to a section of the initial document) significantly exceeds by a threshold amount a next best score for the received section with respect to another section of the initial document. The threshold amount may be a difference between the similarity scores or percentages of at least 20%, but any suitable threshold amount may be utilized. For example:

Version 1 of Document A:
QTc interval <=450 msec for men or <=470 msec for women within 2 weeks of registration.
Version 2 of Document A:
Q-T interval <=450 msec for men or <=470 msec for women within 2 weeks of study.
A similarity score for the section of Version 2 of Document A with respect to the section of Version 1 of Document A may be 92.58%, where a next best similarity score for the section of Version 2 of Document A with respect to another section of Version 1 of Document A may be 57.73%.
Version 1 of Document B:
Histologically or cytologically confirmed HER2-negative breast cancer that is stage IV.
Version 2 of Document B:
Histologically confirmed HER2-negative breast cancer that is stage IV.

A similarity score for the section of Version 2 of Document B with respect to the section of Version 1 of Document B may be 86.09%, where a next best similarity score for the section of Version 2 of Document B with respect to another section of Version 1 of Document B may be 58.83%. In this example case, even though the best similarity score for Version 2 of Document B is less than 90% (as compared to the best similarity score for Version 2 of Document A of 92.58%), the similarity score for Version 2 of Document B significantly exceeds (e.g., 86.09%−58.83%=27.26%) the next best similarity score for the section of Version 2 of Document B with respect to other sections of Version 1 of Document B.

When more than one classification has a score that satisfies the threshold as determined at operation 535, a selection of one of the classifications is performed at operation 540. The selection may include the classification with a score indicating the greatest similarity, differences between the best similarity scores, or a selection by a user.

When a classification is determined (e.g., satisfies the threshold at operation 530 or selected at operation 540), the retrieved section is mapped to the section in the initial document corresponding to the classification at operation 545.

When the classifier does not return a classification with a score satisfying the threshold of similarity as determined at operation 530, the retrieved section is designated as a new section at operation 550.

When additional sections are present in the new document as determined at operation 555, a next section is retrieved at operation 520 and the processing is performed as described above.

Once the sections of the new document have been processed, the presence of any classifications that have not been assigned to a section of the new document is determined at operation 560. When one or more classifications have not been assigned or mapped to a section of the new document, the sections of the initial document that correspond to these unassigned classifications are designated as being removed from the new document at operation 565.

The mapped sections may be utilized for various purposes. For example, the mapped sections may be utilized to produce a history log of the sections over time. By way of further example, the mapped sections between the initial document and new document are compared at operation 570 to determine changes of the content (e.g., text, etc.) of sections in the new document relative to the corresponding sections in the initial document. The sections of the new document may be presented with their corresponding changes on a display at operation 575. The changes may be indicated by various markings (e.g., highlighting, underlining, bold, strikethrough, etc., or any combination thereof). For example, the changes may be highlighted, additional content may be underlined, removed content may include one or more of highlighting (e.g., red or other color) and strikethrough, and new content may be highlighted (e.g., green or other color).

An example operation of a present invention embodiment is described with respect to documents including a policy in the form of the following example medical clinical trial.
Clinical Trial A, Version v1:
a) Patients must be at least 18 years old;
b) Adequate renal function;
c) Patients must be enrolled less than 21 days prior to end of chemotherapy; and
d) Bilirubin levels <2× ULN.

Clinical Trial A, Version v2:
a) Female patients must not be pregnant;
b) Patients must be between 18 and 55 years of age;
c) Patients must be registered less than 21 days prior to end of chemotherapy; and
d) Adequate renal, hematologic, and coagulation function.

An embodiment of the present invention compares the criteria in Version v2 to the criteria in Version v1 of the medical clinical trial as described above in order to determine a difference of the criteria between the versions and identify the following changes:
1. Criterion a) in Version v2 is a brand-new criterion that was not present in Version v1;
2. Criterion b) in Version v2 corresponds to criterion a) in Version v1 (even though the wording changed moderately);
3. Criterion c) in Version v2 corresponds to criterion c) in Version v1 (even though the wording changed slightly);
4. Criterion d) in Version v2 corresponds to criterion b) in Version v1 (even though the wording changed significantly); and
5. Criterion d) in Version v1 is deleted from Version v2.

An example display of the criterion of the medical clinical trial with markings indicating the above changes is illustrated in FIG. 6. By way of example, the markings include underlining additional text, and striking through and highlighting deleted text, where: new criterion a) in Version v2 is highlighted; added content in criteria b) and c) of Version v2 is underlined and highlighted; removed content in criteria b), c), and d) of Version v2 includes strikethrough and highlighting; and removed criteria d) from Version v1 includes strikethrough and highlighting.

Regardless of semantically significant and insignificant differences between the two versions of the trials, a present invention embodiment correctly matches each new criterion to its corresponding entry in the original trial.

Present invention embodiments provide several advantages. For example, the classifier may be trained with a single training instance, thereby reducing processing time and resources to train the classifier. Further, the classifier provides enhanced and intelligent detection of changes and mapping between sections of documents, where the sections may be accurately mapped despite varying degrees of content change (e.g., a few words or characters to sentences, etc.) and change in order or sequence of sections. This reduces significant amounts of comparisons needed to map a new or revised section to a prior section. This further provides quick detection of changes to documents, and enables the detection of changes to documents when fuzzy comparisons are not feasible, and without numerous incremental and/or one to one section comparisons.

It will be appreciated that the embodiments described above and illustrated in the drawings represent only a few of the many ways of implementing embodiments for detecting changes between documents using a machine learning classifier.

The computing environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, change detection module, etc.). These systems may include any types of monitors and input devices (e.g., keyboard, mouse, voice recognition, etc.) to enter and/or view information.

It is to be understood that the software (e.g., change detection module, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., change detection module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., documents, classification information, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information (e.g., documents, detected changes, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., detected changes, history log, etc.).

The present invention embodiments are not limited to the specific tasks or algorithms described above, but may be utilized to detect changes across any quantity of any types of documents including any desired information. The sections may include any quantity or portion of any content of the documents. The changes may be detected across any quantity of documents, where a classifier may be based on any document in the revision sequence to determine changes across any documents in the revision sequence.

The classifier is preferably trained with a single instance of training data for a classification, but may be trained with additional training instances. The classifier may be trained to classify any desired sections of a document, and may provide any indication of similarity or confidence within any desired ranges.

The documents may include any type of individual elements that may be altered for detection of changes (e.g., lists, conditions or criteria, terms, table of contents, chapters with titles, sentences, paragraphs, etc.). The classifier may be implemented by any type of machine learning or other classifier based on the particular application (e.g., types of documents, classifications, etc.). The classifier may further be tuned or trained based on the particular application (e.g., types of documents, classifications, etc.). Any comparisons may be utilized to determine satisfaction of the threshold for similarity (e.g., greater than, greater than or equal to, less than, less than or equal to, etc.), where the similarity score and threshold may be any values in any units (e.g., percentages, dimensionless, etc.), and a higher or lower similarity score may indicate greater similarity based on the implementation.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for detecting changes between documents comprising:
training a machine learning classifier with one or more sections within an initial document to learn classifications for the sections, wherein the one or more sections of the initial document serve as the classifications;
applying one or more second sections of a second document to the machine learning classifier to classify the one or more second sections, wherein at least one second section lacks a classification and indicates a new section relative to the initial document; and
mapping the one or more second sections with a classification to the one or more sections of the initial document based on the classification of the one or more second sections.

2. The method of claim 1, further comprising:
comparing the mapped sections to detect changes within the mapped one or more second sections relative to the one or more sections of the initial document; and
presenting the mapped one or more second sections indicating the detected changes.

3. The method of claim 1, wherein the initial document includes a policy comprising a medical clinical trial.

4. The method of claim 3, wherein the one or more sections include one or more conditions for patients to satisfy to participate in the medical clinical trial.

5. The method of claim 1, wherein at least one classification is unmapped to the one or more second sections of the second document and indicates that a section associated with the at least one unmapped classification is absent in the second document.

6. The method of claim 4, further comprising:
training a plurality of machine learning classifiers each with one or more conditions of a corresponding different policy within a corresponding initial document to learn classifications for the conditions, wherein the one or more conditions of the corresponding initial document serve as the classifications for the corresponding policy;
applying one or more second conditions of a corresponding second document for the corresponding policy to a machine learning classifier associated with the corresponding policy to classify the one or more second conditions; and
mapping the one or more second conditions to the one or more conditions of the corresponding initial document of the corresponding policy based on the classification of the one or more second conditions.

7. A system for detecting changes between documents comprising:
at least one processor configured to:
train a machine learning classifier with one or more sections within an initial document to learn classifications for the sections, wherein the one or more sections of the initial document serve as the classifications;
apply one or more second sections of a second document to the machine learning classifier to classify the one or more second sections, wherein at least one second section lacks a classification and indicates a new section relative to the initial document; and
map the one or more second sections with a classification to the one or more sections of the initial document based on the classification of the one or more second sections.

8. The system of claim 7, wherein the at least one processor is further configured to:
compare the mapped sections to detect changes within the mapped one or more second sections relative to the one or more sections of the initial document; and
present the mapped one or more second sections indicating the detected changes.

9. The system of claim 7, wherein the initial document includes a policy comprising a medical clinical trial, and wherein the one or more sections include one or more conditions for patients to satisfy to participate in the medical clinical trial.

10. The system of claim 7, wherein at least one classification is unmapped to the one or more second sections of the second document and indicates that a section associated with the at least one unmapped classification is absent from the second document.

11. The system of claim 9, wherein the at least one processor is further configured to:
train a plurality of machine learning classifiers each with one or more conditions of a corresponding different policy within a corresponding initial document to learn classifications for the conditions, wherein the one or more conditions of the corresponding initial document serve as the classifications for the corresponding policy;
apply one or more second conditions of a corresponding second document for the corresponding policy to a machine learning classifier associated with the corresponding policy to classify the one or more second conditions; and
map the one or more second conditions to the one or more conditions of the corresponding initial document of the corresponding policy based on the classification of the one or more second conditions.

12. A computer program product for detecting changes between documents, the computer program product comprising one or more computer readable storage media collectively having program instructions embodied therewith, the program instructions executable by at least one processor to cause the at least one processor to:
train a machine learning classifier with one or more sections within an initial document to learn classifications for the sections, wherein the one or more sections of the initial document serve as the classifications;
apply one or more second sections of a second document to the machine learning classifier to classify the one or more second sections, wherein at least one second section lacks a classification and indicates a new section relative to the initial document; and map the one or more second sections with a classification to the one or more sections of the initial document based on the classification of the one or more second sections.

13. The computer program product of claim 12, wherein the program instructions further cause the at least one processor to:

compare the mapped sections to detect changes within the mapped one or more second sections relative to the one or more sections of the initial document; and present the mapped one or more second sections indicating the detected changes.

14. The computer program product of claim 12, wherein the initial document includes a policy comprising a medical clinical trial.

15. The computer program product of claim 14, wherein the one or more sections include one or more conditions for patients to satisfy to participate in the medical clinical trial.

16. The computer program product of claim 12, wherein at least one classification is unmapped to the one or more second sections of the second document and indicates that a section associated with the at least one unmapped classification is absent from the second document.

17. The computer program product of claim 15, wherein the program instructions further cause the at least one processor to:

train a plurality of machine learning classifiers each with one or more conditions of a corresponding different policy within a corresponding initial document to learn classifications for the conditions, wherein the one or more conditions of the corresponding initial document serve as the classifications for the corresponding policy;

apply one or more second conditions of a corresponding second document for the corresponding policy to a machine learning classifier associated with the corresponding policy to classify the one or more second conditions; and map the one or more second conditions to the one or more conditions of the corresponding initial document of the corresponding policy based on the classification of the one or more second conditions.

* * * * *